United States Patent [19]
Missimer

[11] Patent Number: 5,261,250
[45] Date of Patent: Nov. 16, 1993

[54] METHOD AND APPARATUS FOR RECOVERING MULTICOMPONENT VAPOR MIXTURES

[75] Inventor: Dale J. Missimer, San Anselmo, Calif.

[73] Assignee: Polycold Systems International, San Rafael, Calif.

[21] Appl. No.: 28,742

[22] Filed: Mar. 9, 1993

[51] Int. Cl.$^5$ .................... B01D 8/00; A61L 2/00; F25J 1/00
[52] U.S. Cl. .......................................... 62/55.5; 62/9; 62/11; 62/23; 62/40; 422/31; 55/267
[58] Field of Search .................. 62/55.5, 9, 11, 23, 62/40, 36, 292; 422/31; 55/267, 80

[56] References Cited

U.S. PATENT DOCUMENTS

| | | | |
|---|---|---|---|
| 622,936 | 4/1899 | Whiting et al. | |
| 2,242,299 | 5/1941 | Harrington | 62/123 |
| 2,274,094 | 2/1942 | Rupp | 62/175.5 |
| 3,075,362 | 1/1963 | Becker | 62/12 |
| 3,238,633 | 3/1966 | Hackenberg | 34/5 |
| 3,633,371 | 1/1972 | Davison | 62/17 |
| 3,766,714 | 10/1973 | Cunningham et al. | 55/48 |
| 4,249,917 | 2/1981 | Tarancon | 55/48 |
| 4,538,423 | 9/1985 | LeDiouron | 62/55.5 X |
| 4,551,197 | 11/1985 | Guilmette et al. | 62/55.5 X |
| 4,555,251 | 11/1985 | Jonsson et al. | 55/48 |
| 4,666,480 | 5/1987 | Mann | 62/11 |
| 4,668,261 | 5/1987 | Chatzipetros et al. | 62/55.5 X |
| 4,822,563 | 4/1989 | Joslyn | 422/31 |
| 4,954,315 | 9/1990 | Brahmbhatt | 422/31 |
| 5,069,686 | 12/1991 | Baker et al. | 55/16 |
| 5,073,896 | 12/1991 | Reid | 62/55.5 X |
| 5,108,475 | 4/1992 | Briggs | 62/11 |
| 5,128,101 | 7/1992 | Boynton | 422/31 |

FOREIGN PATENT DOCUMENTS 0275472 7/1988 European Pat. Off. ............. 62/55.5

*Primary Examiner*—Henry A. Bennet
*Assistant Examiner*—Christopher B. Kilner
*Attorney, Agent, or Firm*—Owen, Wickersham & Erickson

[57] ABSTRACT

A vapor recovery apparatus which withdraws multicomponent vapor mixtures from processing apparatus (such as gas sterilizers) by condensation at two or more progressively colder levels while maintaining an appropriate balance between components during steps of capture and phase change. Two cold traps provide progressive partial condensation at multiple temperature levels and serve to reduce input energy requirements at least 50% compared to a single cold level. The components in the recovered mixture may include (a) recyclable ozone depleting, global warming and valuable CFCs or HCFCs, (b) hazardous materials and (c) contaminants such as water vapor and air. The system maintains safe balance of component materials by immediately and constantly draining the condensate from a warmer temperature stage into the liquid holding section of a colder trapping zone. The system separates vestigial air or air used as a carrier gas from the condensed mixture, and purges it without an unacceptable release of recyclable materials and also it controls water vapor so that frost or ice can not impair performance. After the cryocondensation procedure, valves isolate the system from the processing apparatus, and the system warms the captured condensate to above room temperature. Warming the condensate pressurizes it for transfer to a vessel used for shipping the captured mixtures for reclaiming and reuse. Opening a drain valve in the second cold trap allows captured condensate to flow from the now higher pressure recovery system to the transport vessel without any mechanical pump.

12 Claims, 1 Drawing Sheet

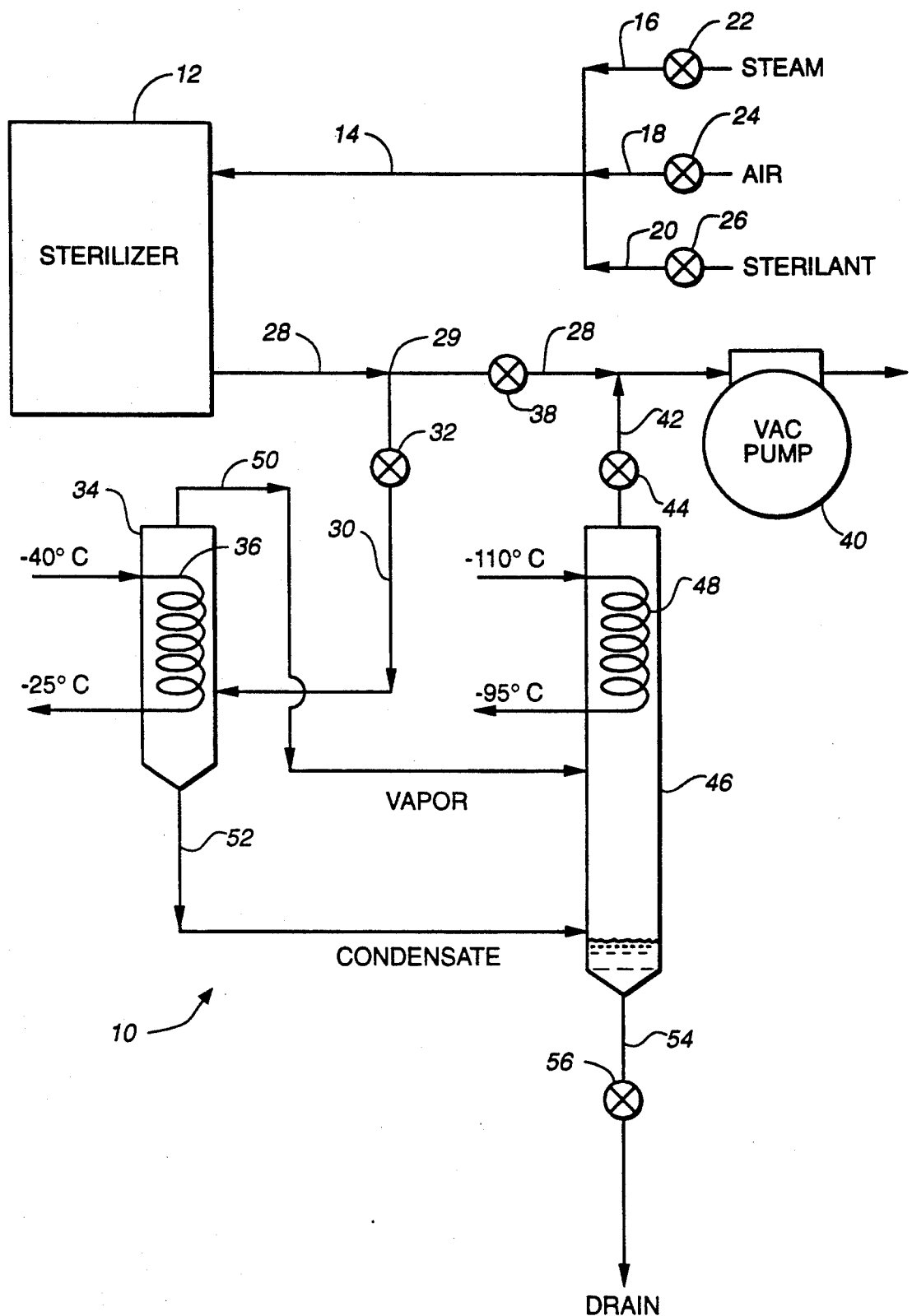

METHOD AND APPARATUS FOR RECOVERING MULTICOMPONENT VAPOR MIXTURES

This invention relates to a method and apparatus for recovering multicomponent vapor mixtures, and more particularly for recovering vapor mixtures used in sterilizing processes.

BACKGROUND OF THE INVENTION

In various industrial processes multicomponent vapor mixtures are used and after their use it may be necessary or highly desirable to capture and recover such mixtures for reuse or to prevent the escape of particularly contaminating constituents to the atmosphere. For example, many hospitals and some industrial manufacturing processes employ a process called gas sterilization which comprises the following steps: (1) A pressure and vacuum sealed enclosure or vessel is loaded with articles to be sterilized. The sterilizer and its contents are preconditioned by evacuation down to a moderately low pressure level, typically about 75 Torr (26 in. Hg Vac.), backfilled with low pressure steam and then re-evacuated. This evacuation-backfill cycle is repeated several times to remove most of the air and to prewarm and moisten the articles to be sterilized. (2) A sterilant gas, typically a 12-88 weight percent mixture of ethylene oxide and CFC-12 (dichlorodifluoromethane), is introduced into the preconditioned and evacuated enclosure until the pressure reaches approximately 1½ atmospheres. This condition is held for a predetermined period adequate to sterilize the articles in the enclosure. Heretofore, the now moist sterilant gas was removed from the enclosure by evacuation and was either discharged into the atmosphere or the sewer. This practice created serious problems. First of all, ethylene oxide by itself is flammable, explosive and toxic, while the blanket vapor, dichlorodifluoromethane or CFC-12 damages the ozone layer in the atmosphere and is a global warming gas. Therefore it became desirable, if not essential, to provide a process for capturing and recovering at least the CFC and preferably both components of the mixture.

The aforesaid problem of capturing the vapor constituents from a sterilizer were further aggravated by the fact that after the initial post-sterilization evacuation step, a continuous air flow at a controlled flow rate was normally introduced into the sterilizer and maintained at slightly below atmospheric pressure. This air wash stream absorbed sterilant gases which desorbed from the sterilized articles and the enclosure's surfaces. Following the previous air wash step, the air flow was stopped, the enclosure evacuated (again, to the atmosphere) and then backfilled with air to slightly less than atmospheric pressure, This air pulse cycle, with a pause each time after backfilling with air, was repeated for a number of cycles or a period of time until the sterilized articles were satisfactorily outgassed.

Because of the explosive potential and toxic risks of ethylene oxide and the ozone depleting characteristics of CFC-12, a satisfactory method for recovering and preventing the release of such sterilizing vapor mixtures became imperative.

The use of several known, conventional types of apparatus and methods for recovering, disposing or otherwise handling multicomponent vapor mixtures have serious disadvantages and have been considered to be impractical.

For example, a procedure entailing the vapor compression then cooling of the vapor mixture to condense it has been suggested. However, in order to attain a high capture rate of around 99%, mechanical evacuation and compression of vapor requires a very high pressure ratio, in excess of 100 to one. High pressure ratios create high discharge temperatures. This may cause deleterious effects when compressing mixtures containing chemically unstable components such as ethylene oxide. This method also lacks the inherent ability to separate significant amounts (more than a few percent) of non-condensible gases such as air at allowable release rates for captured materials. Also, the pumping system may introduce lubricants or other contaminants into recovered materials and requires a high energy input. Therefore, this vapor compression procedure is now used only for those sterilizers which do not employ air for back-filling or air washing but use steam only.

Another suggested method for handling vapor mixtures involved membrane separation of selected vapors. However, membranes are limited to separating specific vapors and must be combined with other technologies, such as catalytic destruction or chemical scrubbing, to adequately process mixtures for desired recovery. Also, their useful life may be limited and require periodic replacement.

Similarly, the use of sorption onto charcoal or molecular sieves has been considered, but sorption, at ambient, low or cryogenic temperatures, has similar limits as those for membranes. Sorbents can become polluted or create acidic conditions and hence less effective over a number of cycles of use and require significant maintenance or replacement.

Cryogenic condensing and separation of recyclable materials was another possible approach to the problem of handling vapor mixtures. However, expendable cryogens, e.g. liquid nitrogen, require special transportation, handling and sometimes logistics problems, thereby entailing high operating costs, and some attendant safety risks. Such cryogens also require supplemental separation techniques particularly for removal of components which freeze well above nitrogen's boiling point.

Catalytic destruction of combustible components is another vapor handling technique, but catalytic disposer units can only remove combustible portions of mixtures and therefor must be used in combination with other apparatus such as membranes or scrubbers. Also, they cannot dispose of nor convert CFCs into benign materials, and the method in general requires a high energy input.

Chemical (typically acid) scrubbing of vapors to remove and render benign selected components is a well know process used for vapor control, but scrubbers remove only those components with which the chemical reacts. Other components such as halocarbons require additional apparatus for recovery.

In summary, all the above prior methods and apparatus considered for handling the moist vapor mixtures such as those used in sterilizers entailed serious disadvantages and failed to solve the problem.

It is therefore one object of the present invention to provide an apparatus and method for capturing multicomponent mixtures existing only in a vapor phase, including ozone depleting and possibly hazardous materials, and for recovering and/or recycling, such mixtures comprising condensible vapors, non-condensible air, moisture or their contaminants.

Another object of the invention is to provide an apparatus for recovering multicomponent vapor mixtures which significantly reduces the required energy input (by at least 50% compared to a single cryogenic temperature capture system) while retaining a capture efficiency of at least 99% for a vapor mixture such as OxyFume-12 (88% R-12 and 12% by weight ethylene oxide) starting at a dew point as low as −15 C. and mixed with water vapor and air.

Another object of the invention is to maintain a safe balance between the blanketing vapor and the toxic or hazardous components of a mixture, e.g. the R-12 and ethylene oxide of the above example, during all stages of capture.

Other objects of the invention are to provide a method and apparatus for recovering multicomponent vapor mixtures which: (1) separates benign non-condensible gases (e.g. air) from recyclable materials and safely disposes of such gases without an unacceptable release of captured components; (2) extracts hazardous, environmentally undesirable or valuable vapors from their point of use and transfers them in either liquid or vapor phases as required, from the recovery system to vessels for transport and reclamation, without using mechanical pumping means that might introduce contamination; (3) provides a capture efficiency of at least 99% for a mixture comprising 88% (weight) CFC-12 and 12% ethylene oxide; and (4) is able to operate properly under any of three distinct modes: (a) Evacuating the source enclosure from an initial pressure of one to two atmospheres, when it contains almost all condensible materials with little non-condensible air present, down to a vacuum; (b) Pumping out (evacuating) the source enclosure after it has been backfilled with air, the air serving as a carrier gas for both the residual vapors in the apparatus and vapors desorbed from products within the apparatus, and therefore to separate and capture condensible vapors at a low concentration in the mixture, and (c) Removing condensible vapors from a steady flow of a carrier gas, typically air, flowing at a steady rate from the source enclosure to the recovery system; and comprising a compact integrated recovery system capable of achieving the above objectives at lower total (acquisition, installation and operating) cost and lower energy requirements than other prior art technologies.

BRIEF SUMMARY OF THE INVENTION

In accordance with the principles of the invention the aforesaid objects are accomplished by an apparatus which can be connected directly to a chamber such as a medical instrument sterilizer which contains the vapor mixture that is to be recovered. An outlet conduit from the mixture chamber or sterilizer has a first branch conduit through a capture valve to a first level cooling tank or cold trap. This outlet conduit also connects to one side of a precondition valve whose other side is connected to a vacuum pump. Between the precondition valve and the vacuum pump is another branch conduit connected to a second cooling tank or cold trap, preferably at a lower level. The upper end of the first cooling tank or cold trap is connected by a vapor transporting conduit to the second cooling tank. The lower end of the first cooling tank is connected to a conduit which transports condensate by gravity flow to the second cooling tank. The first cooling trap has an internal coil or cooling surface which is cooled by a first outside refrigerant source to an operating temperature range of −5 to −40 C. and the second cold trap assembly has an internal coil which is cooled to a range of −95 to −110 C. After a normal sterilization process wherein the sterilizer is filled with a vapor mixture of steam, ethylene oxide and CFC-12, the vapor mixture is drawn directly into the apparatus by a cryo pumping action and a vacuum pump. With the preconditioning valve closed and the capture valve open, the moist sterilant vapor mixture flows into the first cold trap which is at a low pressure. Volatile vapors start condensing on the coil of the first cold trap and the steam condenses as frost. The sterilant vapor, a mixture of two compounds, partially condenses within the first cold trap. The condensate formed in the first cold trap is drained into the reservoir section of the second trap. The colder coil or cryosurface in the second trap induces flow of uncondensed vapor from the first cold trap to the second cold trap and this vapor is ultimately condensed on the colder coil. The condensed vapor from this coil blends with the condensate from the first trap in the reservoir of the second trap and hence the condensed sterilant mixture promptly returns to its original safe ratio of the blanket material, CFC-12, to ethylene oxide. Thus, this reconstituted mixture can be transported for reuse without being dumped into the atmosphere.

Other objects, advantages and features of the invention will become apparent from the following detailed description of a preferred embodiment thereof, presented in conjunction with the accompanying drawing

BRIEF DESCRIPTION OF DRAWING

The attached drawing is a diagrammatic representation of an apparatus embodying principles of the invention.

DETAILED DESCRIPTION OF EMBODIMENT

With reference to the drawing a recovery apparatus 10 is shown which withdraws a multicomponent vapor mixture from a processing chamber which, in the example shown, is a gas sterilizer 12. Such sterilizers are commonly used in hospitals and laboratories for sterilizing surgical implements and the like. In use, as previously described, the sterilizer is filled with a sterilant gas, typically a 12–88 weight percent mixture of moist ethylene oxide and CFC-12 (dichlorodifluoromethane). As described below, the apparatus 10 functions to remove and recover the gas mixture from the sterilizer and to provide a condensate end product comprised of the original mixture constituents in substantially the same proportions as when first supplied to the sterilizer.

Connected to the sterilizer 12 is an input conduit 14 which in turn is connected to three supply inputs 16, 18 and 20 for admitting either steam, air or sterilant to the sterilizer. Each input has its own supply valve 22, 24 or 26 for controlling flow from a separate supply source (not shown).

An output fluid conduit 28 extends from the sterilizer to carry the moist gas mixture from it. This conduit is connected through a first or precondition valve 38 to a vacuum pump 40. Branching from conduit 28 at a junction 29 is a conduit 30 which passes through a controllable second or capture valve 32 and extends to a first cooling chamber or trap 34. This trap has within it a coil 36 providing a cooling surface, the ends of which extend out from the cooling trap 34. The ends of the coil 36 are connected to a suitable refrigerant source (not shown) which is capable of supplying refrigerant to the coil in a temperature range of −5 to −40 degrees C. Such a refrigeration source may be an apparatus such as shown in U.S. Pat. No. 3,768,273.

At a short distance from the junction 29, the conduit 28 is connected through the precondition valve 38 and thereafter to the vacuum pump 40. Connected to the conduit 28 between the valve 38 and the pump 40 is a branch conduit 42 which extends through a third valve 44 from a second cooling chamber or trap 46. This trap is preferably situated lower than the first cooling trap 34. Within the trap 46 is a cooling coil 48 whose ends extend outside the trap to a refrigeration source (not shown) which furnishes refrigerant to the cool 48 at a temperature range of −95 to −110 degrees C. Such a refrigeration source may be of the type shown in the previously mentioned U.S. Patent.

A conduit 50 for carrying vapor from cooling trap 34 is connected to the upper end thereof and extends to cooling trap 46, preferably at a location just below its cooling coil 48.

To the bottom end of the cooling trap 34 a conduit 52 is connected for carrying condensate therefrom. The other end of this condensate conduit is connected to the lower, colder cooling trap 46 near its bottom or reservoir end so that condensate will flow from trap 34 to trap 46 by gravity.

Extending from the conical or dished shaped lower end of cooling trap 46 is a conduit 54 having a drain valve 56 for removing the reclaimed condensate from the apparatus 10.

The detailed operation and method employed by the apparatus 10 will now be described together with an explanation of a typical sterilization process.

Sterilization Process

For preconditioning, sterilizer 12 first is evacuated by vacuum pump 40 via conduit 28 and through precondition valve 38. Following this, valve 38 then is closed. Steam is now admitted into sterilizer 12 via conduits 16 and 14 through valve 22. When sterilizer 12 reaches a predetermined pressure, steam valve 22 is closed and preconditioning valve 38 is reopened for a repeat of the evacuation step. After several such cycles and then a last evacuation step, valve 26 opens to admit sterilant gas into sterilizer 12 via conduits 20 and 14 until the sterilant's pressure reaches a predetermined pressure equivalent to a dew point of about −10 to −15 C. The gas then sterilizes the implements or products therein. After the sterilization cycle, the recovery system begins its capture of the gases and vapors for reclaiming and recycling.

Capture System Preconditioning

During or before the sterilizer's preconditioning and sterilizing steps, trapping (condensing) coils or surfaces 36 and 48 in cold trap assemblies 34 and 46 are precooled to operating temperature levels, between −5 to −40 C. and −95 to −110 C. respectively. Vacuum pump 40 purges air from cold trap assemblies 34 and 46 via conduit 42 and evacuation valve 44 any time a significant amount of air accumulates.

Air Purge

Accumulated air is detected by (a) measuring the temperature of cryogenic surface 46, (b) calculating the sterilant's vapor pressure at this temperature and (c) comparing this pressure to the pressure within cold trap assembly 46. The difference between the pressure in the cold trap and the vapor pressure at cryosurface temperature of cryosurface 46 indicates the partial pressure of air present. Vacuum pump 40 withdraws the air via conduit 42 and through evacuation valve 44 until the two pressures are near each other. The evacuated air carries only trace amounts of sterilant vapor out of cold trap assembly 46 to the vacuum pump 40 because of the cryogenic temperature and geometry of the cryosurface 48 which permits only minimal bypass flow.

Capture Cycle

After the sterilizer 12 completes its sterilization cycle and with supply valves 22, 24 and 26 preconditioning valve 38 closed, the capture valve 32 is opened. A mixture of moist sterilant vapor and residual air flows from the sterilizer 12 via conduits 28 and 30 into cold trap assembly 34 which is at low pressure. Volatile vapors start condensing on the cryosurface 36. Almost all of the steam (water vapor) condenses in the form of frost on surface 36. The sterilant vapor, a mixture of two compounds which do not form an azeotrope, partially condenses. The condensate is richer in the higher boiling component, ethylene oxide, and vapor is richer in the more volatile (lower boiling) component, typically a blanketing vapor such as CFC-12. The condensate formed in cold trap 34 drains via conduit 52 to the reservoir section of cold trap 46. Cryosurface 48 in cold trap 46, which is at a very low temperature, induces flow of the uncondensed vapor and residual air from cold trap 34 via conduit 50 to cold trap 46. There this vapor condenses on cryosurface 48 and drops into and blends with the condensate from cold trap 34 in the reservoir section of cold trap 46. Thus, the condensed sterilant mixture promptly returns to its original safe ratio of CFC-12 to ethylene oxide.

Air Pulse

Capture valve 32 is closed to isolate sterilizer 12 from the capture system. Air admitting valve 24 is opened to backfill sterilizer 12 with air to nearly one atmosphere pressure and then is closed. Sterilant vapor and moisture, now desorbing from the sterilized products and the walls of the sterilizer 12, diffuse into the air. After a predetermined time, air admitting valve 24 is closed and capture valve 32 is opened. The capture system then removes this air and moist sterilant mixture in the same manner as described above except that the fluid flowing is now principally air. Cold trap 34 precools this fluid stream to almost the temperature of cryosurface 36 with little or no condensation of volatiles because of their low partial pressure. This fluid stream flows via conduit 50 to cold trap 46 where its cryosurface 40 removes by condensation volatile vapors due to its very low temperature. Vacuum pump 40 removes the air, now essentially free of sterilant, via conduit 42 and through evacuation valve 44. A predetermined number of these air pulse cycles may be repeated or an air wash cycle may follow.

Air Wash

This cycle is similar to the air pulse described above except that when the sterilizer 12 is backfilled with air until it reaches a pressure just below one atmosphere, air admitting valve 24 remains open when the capture valve 32 is opened. A controlled flow of air flows into the sterilizer and vacuum pump 42, with evacuation valve 44 open, operates continuously for a predetermined period. This optional process provides a flushing process for removal of absorbed sterilant from sterilized products and sterilizer 12. Air admitting valve 24 closes at the end of the air washing period and the capture system and vacuum pump 40 continue to operate for removal of residual air and vapors from sterilizer 12. Additional air pulse cycles may follow the air wash cycle as determined necessary to remove residual sterilant vapors from sterilizer 12 and the sterilized products therein.

Recovery and Transfer

After completion of the capture processes, capture valve 32 and air purge valve 44 are closed to isolate the captured moist sterilant condensate within the capture system. The condensate in the reservoir section of cold trap 46 and cryosurfaces 36 and 48 are heated to above room temperature until the pressure of the condensate increases to a suitable level for transfer. The heat source can be electric resistance heaters. A preferred embodiment is a modified version of U.S. Pat. No. 4,535,597. This arrangement utilizes heat rejected from the cooling system to quickly reheat a cryogenic surface. (See Cooling System described below). A transport cylinder, not shown, is connected to drain valve 56. Drain valve 56 and the cylinder's valve are opened to allow transfer of the now warm (moist and used) sterilant liquid via conduit 54 from the capture system to the cylinder. Drain valve 56 and the cylinder valve are closed and the capture cycle is ready to be repeated.

Energy Savings

Dividing the cold trapping process into two temperature levels or steps reduces the required input power by at least one-half. Energy is saved because a large portion of the heat load for condensing the mixture is handled at warmer temperatures. More than one-half the sensible and latent heat (cooling) energy required for the total cold trapping effect is above about −30 C. with the remainder between −30 C. and −95 to −105 C. The input power required for the same refrigeration effect at the colder level of about −100 C. is three times as great as at the warmer level of −30 C.

Safety and Condensate Management

Trapping in two steps creates two condensate streams. It might be considered more logical to keep these condensate streams separate until transferring the captured materials into storage or shipping containers. However, ethylene oxide is a hazardous material and will burn or explode when exposed to air and not mixed with enough blanketing gas to make the mixture safe. The arrangement of the present invention which provides two temperature level trapping serves to fractionate the CFC-12 and ethylene oxide mixture causing condensate from the warmer trap to be rich in ethylene oxide and that from the colder trap to be rich in CFC-12. Thus, a hazardous situation could exist if air somehow was mixed with the condensate from the warmer trap. This potential problem is solved in a novel way by promptly draining this condensate into the colder trap where the two condensate streams mix and the remaining vapors are rich in the blanketing material. The extra cooling required to subcool the warmer condensate to the colder trap temperature is not significant because it is only sensible heat without a phase change. In this manner, a safe balance of the component materials is maintained throughout the two step trapping process.

Cooling System

A number of refrigerating systems can be employed for refrigerating the cold traps 34 and 46 in this trapping system 10. Expensive expendable cryogens require constant transport and handling and therefore are not best suited. A single stage vapor compression refrigerator can cool the −30 C. trap and a conventional multi-compressor cascade system can, with difficulty, produce the necessary cooling for the −95 to −110 C. trap. A preferred cooling system is described in U.S. Pat. No. 3,768,273. FIG. 1 in this patent illustrates two refrigerant evaporators, 28 and optional 51, which operate at lowest and intermediate temperatures respectively. Such a system provides the required cooling and, when modified as mentioned the Recovery and Transfer section above, it can provide the required reheating for transfer of the captured materials. In this manner, no mechanical pumps are needed to move and possibly contaminate captured sterilant.

While the foregoing apparatus 10 is particularly adapted for reclaiming a sterilant gas mixture, the principles of the present invention could also be applied for reclaiming gas or vapor mixtures with various constituents used in other devices.

To those skilled in the art to which this invention relates, many changes in construction and widely differing embodiments and applications of the invention will make themselves known without departing from the spirit and scope of the invention. The disclosure and the description herein are purely illustrative and are not intended to be in any sense limiting.

What is claimed is:

1. An apparatus for recovering a mixture of chemical compounds used as a vapor mixture in predetermined proportions of said compounds within a chamber, said apparatus comprising:
   a main fluid conduit extending from said chamber, through a first valve and connected at its outer end to a vacuum pump;
   a first branch conduit extending from said main conduit through a second valve;
   a first cold trap connected to said first branch conduit
   first cryosurface means within said first cold trap and connected to a first low temperature refrigerant source;
   a second cold trap and a second cryosurface means within said second cold trap which is connected to a second low temperature refrigerant source that circulates refrigerant thereto at a lower temperature than said first refrigerant source;
   a second branch conduit extending from said second cold trap through a third valve to said main fluid conduit;
   a vapor conduit interconnecting said cold traps for carrying vapor from said first trap to said second trap; and
   a condensate conduit connected to the lower end of said first cold trap for conveying condensate to said second trap.

2. The apparatus as described in claim 1 wherein said vapor mixture is comprised of a sterilant material and a blanketing material.

3. The apparatus as described in claim 2 wherein said vapor mixture comprises almost 12% by weight of ethylene oxide and about 88% by weight of CFC-12

4. The apparatus as described in claim 1 wherein said first refrigerant source maintains said first cryosurface means within a temperature range of −5° C. to −40° C. and said second refrigerant source maintains said second cryosurface means within a temperature range of −95° C. to −110° C.

5. The apparatus as described in claim 1 wherein said first and second cold traps each comprise upright cylindrical chambers and said second trap is situated at a level below that of said first trap.

6. The apparatus as described in claim 5 wherein said first and second cryosurface means are fluid conduit coils located within said first and said cold traps, respectively.

7. The apparatus as described in claim 2 including:
an input conduit connected to said chamber;
supply conduits connected to said input conduit extending from separate sources of steam, air and sterilant material; and a shut-off valve in each said supply conduit.

8. A method for recovering a vapor mixture of chemical compounds used in an enclosed chamber, said method comprising the steps of:
providing a recovery apparatus for drawing the mixture from said chamber into a first cold trap;
cooling the mixture in said first cold trap to a first temperature level which causes partial condensation of said mixture.
draining condensate from said first cold trap to a second cold trap;
drawing vapor from said first cold trap into said second cold trap;
cooling said second cold trap to a temperature level that is lower than said first cold trap so that all vapor therein is condensed and combines with condensate from said first cold trap; and
draining the combined condensate from said second cold trap for storage or reuse.

9. The method of claim 8 wherein said first cold trap is cooled to a temperature range of −5° to −40° C. and said second cold trap is cooled to a temperature range of −95° C. to −110° C.

10. The method as described in claim 8 wherein said enclosed chamber is a sterilizer and said vapor mixture is comprised of ethylene oxide and CFC-12.

11. The method of claim 8 including the further steps of:
heating the combined condensate to above room temperature until the pressure of the condensate increases to a suitable level for transfer to a storage container.

12. The method of claim 8 including the steps of:
providing a valve for isolating the enclosed chamber from the recovery apparatus;
closing said valve after all of the vapor has been drawn from said chamber;
allowing additional vapor and moisture to desorb from products and walls within said chamber over a predetermined time period;
opening said valve after said time period;
admitting a pulse of air into said chamber to remove therefrom said desorbed additional vapor and moisture and force it into the recovery system to condense the additional vapor.

* * * * *